United States Patent [19]

Bacon et al.

[11] Patent Number: 5,466,433
[45] Date of Patent: Nov. 14, 1995

[54] POLYIODINATED AROYLOXY ESTERS

[75] Inventors: Edward R. Bacon, Audubon, Pa.; Sol J. Daum, Albany; Paul P. Spara, Fairport, both of N.Y.

[73] Assignee: Eastman Kodak Company, Rochester, N.Y.

[21] Appl. No.: 261,794

[22] Filed: Jun. 20, 1994

Related U.S. Application Data

[63] Continuation-in-part of Ser. No. 990,987, Dec. 16, 1992, Pat. No. 5,322,679.

[51] Int. Cl.⁶ ............................................. A61K 49/04
[52] U.S. Cl. ......................... 424/9.451; 560/47; 560/83
[58] Field of Search ............................. 560/47, 83; 424/5

[56] References Cited

U.S. PATENT DOCUMENTS

| | | |
|---|---|---|
| 3,097,228 | 7/1963 | Larsen . |
| 3,144,479 | 8/1964 | Obendorf . |
| 3,317,569 | 5/1967 | Larsen et al. .................... 260/347.4 |
| 4,924,009 | 5/1990 | Neckers et al. ................... 549/223 |
| 5,322,679 | 6/1994 | Bacon et al. ......................... 424/5 |

FOREIGN PATENT DOCUMENTS

| | | |
|---|---|---|
| 241516 | 11/1962 | Australia . |
| 0498482A1 | 1/1992 | European Pat. Off. . |
| 866184 | 4/1961 | United Kingdom . |

OTHER PUBLICATIONS

CA 109:128247, 1987.
CA 107:133706, 1986.
CA 106:83870, 1985.
Obendorf, W., Chem. Abstract, 57:4603i (1962)
Siggens et al, J. Med. Chem., 8(5), pp. 728-730 (1965).

*Primary Examiner*—José G. Dees
*Assistant Examiner*—Samuel L. Barts
*Attorney, Agent, or Firm*—Arthur H. Rosenstein

[57] ABSTRACT

Compounds having the structure

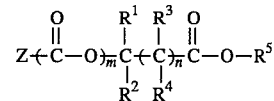

wherein $Z\text{-}(COO\text{-})_m$ is the residue of a polyiodinated aromatic acid;

m is 1, 2, 3 or 4;

n is an integer from 1 to 20;

$R^1$ and $R^2$ are independently H, alkyl, fluoroalkyl, cycloalkyl, aryl, aralkyl, alkoxy or aryloxy;

$R^3$ and $R^4$ are independently H, alkyl, fluoroalkyl, cycloalkyl, aryl, aralkyl, alkoxy, aryloxy, halogen, hydroxy or acylamino; and $R^5$ is H, alkyl, cycloalkyl, aryl, aralkyl, alkoxyalkyl or acetamidoalkyl;

are useful as contrast agents in x-ray imaging compositions and methods.

9 Claims, No Drawings

POLYIODINATED AROYLOXY ESTERS

This application is a continuation-in-part of U.S. patent application Ser. No. 07/990,987 filed Dec. 16, 1992 now U.S. Pat. No. 5,222,679.

FIELD OF INVENTION

This invention relates to polyiodinated aroyloxy esters which are particularly useful as contrast agents for x-ray imaging.

BACKGROUND OF THE INVENTION

X-ray imaging is a well known and extremely valuable tool for the early detection and diagnosis of various disease states in the human body. The use of contrast agents for image enhancement in medical x-ray imaging procedures is widespread. An excellent background on iodinated and other contrast agents for medical imaging is provided by D.P. Swanson et al, *Pharmaceuticals in Medical Imaging*, 1990, MacMillan Publishing Company.

U.S. Pat. No. 3,097,228 describes derivatives of 2,4,6-triiodobenzoyloxyalkanoic acids having the structure

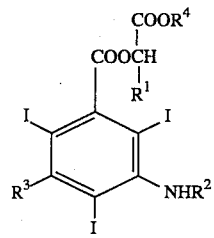

wherein $R^1$ is H or lower alkyl; $R^2$ is H or lower-alkanoyl; and $R^3$ is H or lower alkanoylamino and $R^4$ is lower alkyl.

U.S. Pat. No. 3,144,479 describes iodinated benzoic acid esters having the formula

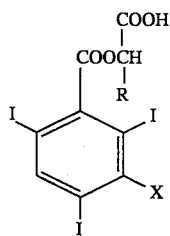

wherein X is an iodine atom or an amino group and R is selected from H, alkyl, alkoxyalkyl, i.e., $-(\overline{CH_2})_m-O-R''$, wherein R'' is alkyl and m is 1 or 2, phenyl and a particular iodinated aromatic group.

Obendorf (Chem. Abstract 57:4603i) discloses the compound

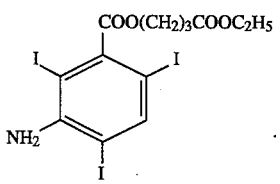

However, this compound has an unacceptably low melting point to be suitably formulated in nanoparticulate x-ray contrast compositions.

Siggins et al (J. Med. Chem. 8(5), 728–30 (1965)) describe iodobenzoates for myelography. However, all of the described compounds are monoiodobenzoates containing less than 40% iodine by weight intended to be intracisternally administered as an oil.

EP-A 498,482 describes nanoparticulate x-ray contrast compositions which have proven to be extremely useful in medical imaging. However, particulate contrast agents in certain in vivo applications can exhibit less than fully satisfactory solubility profiles and/or enzymatic degradation, e.g., in plasma and blood.

It would be desirable to provide compounds for use as x-ray contrast agents having improved enzymatic degradability and appropriate solubility profiles.

SUMMARY OF THE INVENTION

We have discovered and prepared novel polyiodinated aroyloxy esters which are useful as contrast agents in x-ray imaging compositions and methods.

More specifically, in accordance with this invention, there are provided uncharged compounds having the structure

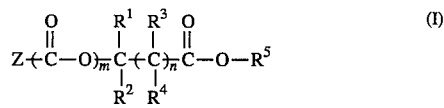

wherein $Z-(COO)_m$ is the residue of a polyiodinated aromatic acid;

m is 1, 2, 3 or 4;

n is an integer from 1 to 20;

$R^1$ and $R^2$ are independently H, alkyl, fluoroalkyl, cycloalkyl, aryl, aralkyl, alkoxy or aryloxy;

$R^3$ and $R^4$ represents individual COO units attached to Z are independently H, alkyl, fluoroalkyl, cycloalkyl, aryl, aralkyl, alkoxy, aryloxy, halogen, hydroxy or acylamino; and $R^5$ is H, alkyl, cycloalkyl, aryl, aralkyl, alkoxyalkyl or acetamidoalkyl.

This invention further provides an x-ray contrast composition comprising the above-described compound and a method for medical x-ray diagnostic imaging which comprises administering to the body of a test subject an effective contrast producing amount of the above-described x-ray contrast composition.

It is an advantageous feature of this invention that novel compounds are provided which find particular utility as x-ray contrast agents.

It is another advantageous feature of this invention that compounds are provided having improved enzymatic degradability and appropriate solubility profiles.

DESCRIPTION OF PREFERRED EMBODIMENTS

In structural formula I above, $Z-(COO)_m$ is the residue of a polyiodinated aromatic mono- or poly-acid. m is 1, 2, 3 or 4. In preferred embodiments, m is 1 or 2. The iodinated aromatic acid can comprise two, three or more iodine atoms per molecule. Preferred species contain at least two iodine atoms per aromatic ring. The iodinated compounds can contain substituents which do not deleteriously effect the contrast enhancing capability of the compound.

Illustrative examples of preferred polyiodinated aromatic mono- and di-acids include
diatrizoic acid,
metrizoic acid,
urokonic acid,
2,4,6-triiodo-5-acetylamino-isophthalic acid,
iothalamic acid,
triiodotrimesic acid,
ioxaglic acid (hexabrix),
ioxitalamic acid,
tetraiodoterephthalic acid,
iocarmic acid,
iodipamide, and the like.

In preferred embodiments, Z—(COO—)$_m$ is the residue of a substituted triiodobenzoic acid such as an acyl, carbamyl, and/or acylamino substituted triiodobenzoic acid. In highly preferred embodiments, Z—(COO—)$_m$ is the residue of a polyiodinated aromatic acid such as diatrizoic acid, metrizoic acid, urokonic acid, 2,4,6-triiodo-5-acetylamino-isophthalic acid or iodipamide.

n is an integer from 1 to 20. In certain preferred embodiments, n is an integer from 4 to 20.

$R^1$ and $R^2$ independently represent H; linear or branched alkyl, preferably containing from 1 to 20, more preferably 1 to 8 carbon atoms such as methyl, ethyl, propyl, isopropyl, butyl, pentyl, hexyl and the like; fluoroalkyl, the alkyl portion of which is as described above and containing from 1 to (2m+1) fluorine atoms (where m=the number of carbon atoms in the alkyl group), such as trifluoromethyl; cycloalkyl, preferably containing from 3 to 8 carbon atoms such as cyclopropyl, cyclobutyl, cyclopentyl and cyclohexyl; aryl, preferably containing from 6 to 10 carbon atoms, such as phenyl and naphthyl; aralkyl, preferably containing from 7 to 12 carbon atoms, such as benzyl; alkoxy, the alkyl portion of which contains from 1 to 20 carbon atoms as described above; or aryloxy, the aryl portion of which preferably contains from 6 to 10 carbon atoms as described above.

$R^3$ and $R^4$ independently represent a substituent as defined for $R^1$ above; halogen, such as chlorine, bromine or iodine; hydroxy; or acylamino, i.e., a

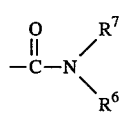

group wherein $R^6$ and $R^7$ are independently H, alkyl, aryl, aralkyl or alkoxy as defined for $R^1$ above, acetamidoalkyl, i.e.,

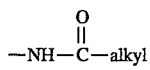

wherein alkyl is as defined for $R^1$ above, —COO—alkyl, the alkyl portion of which is as defined for $R^1$ above, cyano and the like, or $R^6$ and $R^7$ taken together with the nitrogen atom to which they are attached, represent a 4–7 membered saturated or unsaturated nitrogen containing ring such as piperidyl, piperizinyl, pyrrolidinyl, and the like. However, reactive substituents such as halogen, hydroxy, and acylamino are not preferred on carbon atoms adjacent to the ester groups.

$R^5$ represents H, alkyl as defined for $R^1$ above; cycloalkyl as defined for $R^1$ above; aryl as defined for $R^1$ above, aralkyl as defined for $R^1$ above; alkoxy, as defined for $R^1$ above; aryloxy, as defined for $R^1$ above; alkoxyalkyl, the alkyl and alkoxy portions of which are as defined for $R^1$ above; or acetamidoalkyl; i.e.,

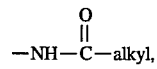

wherein alkyl is as defined for $R^1$ above.

In preferred embodiments, the compounds of this invention have the structure

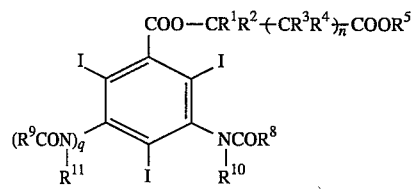

or

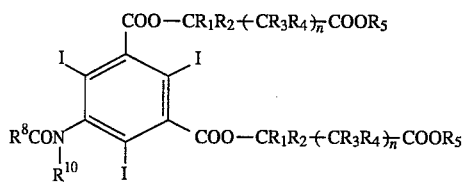

wherein $R^1$, $R^2$, $R^3$, $R^4$, $R^5$ and n are as defined above; q is 0 or 1;

$R^8$ and $R^9$ are independently alkyl, as defined for $R^1$ above, cycloalkyl, as defined for $R^1$ above, aryl, as defined for $R^1$ above, or aralkyl, as defined for $R^1$ above; and $R^{10}$ and $R^{11}$ are independently H or —COR$^8$, wherein $R^8$ is as defined above.

In other preferred embodiments, the compounds of this invention have the structure

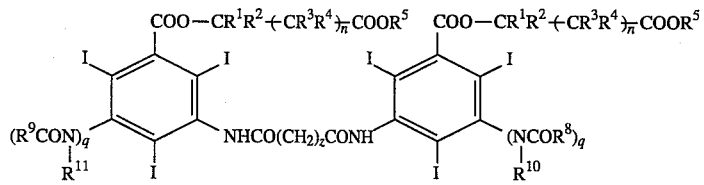

wherein z is an integer from 1 to 10, and $R^1$, $R^2$, $R^3$, $R^4$, $R^5$, $R^8$, $R^9$, $R^{10}$, $R^{11}$, q and n are as defined above.

The alkyl, cycloalkyl, aryl, aralkyl and alkoxy groups in structure I above can be unsubstituted or substituted with various substituents which do not adversely affect the stability or efficacy of the compounds as x-ray contrast agents such as alkyl, cycloalkyl, aryl, aralkyl, alkoxy, hydroxy, acyloxy, halogen, such as chlorine, bromine and iodine, acylamino, carboalkoxy, carbamyl and the like. However, reactive substituents such as halogen are not preferred on the carbon atoms, if present, adjacent to the ester group.

The compounds of this invention can be prepared by contacting the carboxylate of an iodinated aromatic acid with a functionalized ester having the formula

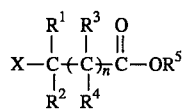

wherein X is a leaving group and n and $R^1$–$R^5$ are as defined above, in a suitable solvent. Suitable leaving groups include halogen, such as Br, I and Cl, sulfonyloxy, such as methanesulfonyloxy and toluenesulfonyloxy. Suitable solvents include dimethylformamide. The carboxylates of iodinated aromatic acids and functionalized esters useful as the starting materials in the preparation of the compounds of this invention are known compounds and/or can be prepared by techniques known in the art. For example, suitable esters include commercially available bromoesters and chloroesters derivatives as exemplified below. A general reaction scheme is as follows:

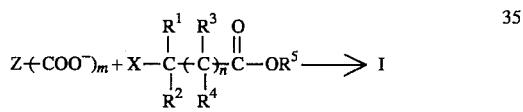

The reaction can take place at various temperatures ranging between −78° C. and 100° C., and preferably −40° C. and 50° C. For convenience, the reaction can take place at ambient pressure, however, higher and lower pressures are contemplated.

The reaction can take place in any suitable solvent. Suitable solvents include N,N-dimethylformamide and dimethylsulfoxide. A particularly preferred compound of this invention is WIN 69979 having the structure;

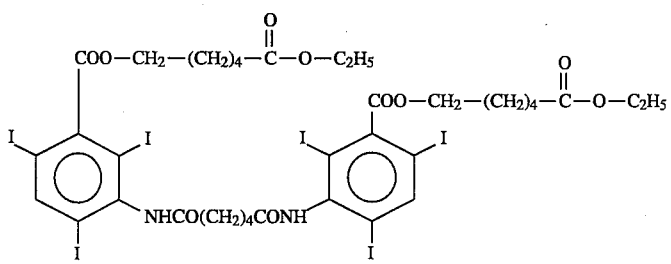

Other preferred compounds of this invention conform to structure I above, wherein $R^1$–$R^4$=H as indicated below:

| WIN | Z | n | m | R⁵ |
| --- | --- | --- | --- | --- |
| 67722 | ![structure: 2,4,6-triiodo-1,3-bis(acetamido)benzene with CH₃CONH and NHCOCH₃ groups] | 4 | 1 | $C_2H_5$ |
| 67954 | " | 3 | 1 | $C_2H_5$ |
| 67995 | " | 4 | 1 | $CH(CH_3)_2$ |
| 68039 | " | 4 | 1 | $CH_2OCOC(CH_3)_3$ |
| 68061 | " | 2 | 1 | $C_2H_5$ |
| 68060 | " | 2 | 1 | $CH_2-C_6H_5$ |
| 68136 | " | 5 | 1 | $C_2H_5$ |
| 68166 | " | 6 | 1 | $C_2H_5$ |
| 70467 | " | 4 | 1 | $CH_3$ |
| 71300 | " | 4 | 1 | $CH_2CH(CH_3)_2$ |
| 72313 | " | 4 | 1 | $C(CH_3)_3$ |
| 68767 | ![structure: triiodobenzene with CH₃COHN and N(COCH₃)(CH₃) groups] | 4 | 1 | $C_2H_5$ |
| 68888 | " | 3 | 1 | $C_2H_5$ |
| 68384 | ![structure: triiodobenzene with NHCOCH₃] | 4 | 1 | $C_2H_5$ |
| 68038 | ![structure: triiodobenzene with (CH₃CO)₂N and N(COCH₃)₂] | 4 | 1 | $C_2H_5$ |
| 22256 | ![structure: triiodo-methyl benzene with CH₃COHN] | 2 | 2 | $C_2H_5$ |
| 69732 | " | 4 | 2 | $C_2H_5$ |
| 69943 | ![structure: bis(triiodophenyl) linked by NHCO(CH₂)₄CONH] | 2 | 2 | $C_2H_5$ |
| 69944 | " | 3 | 2 | $C_2H_5$ |
| 69979 | " | 4 | 2 | $C_2H_5$ |

When used as an x-ray contrast agent, the compounds of this invention preferably comprise at least about 40%, more preferably at least 45% iodine by weight.

In preferred embodiments, the compounds of this invention can be formulated into particulate x-ray contrast compositions, preferably nanoparticulate x-ray contrast compositions, as described in commonly-owned EP-A 498,482. Preferred compounds for this application have a melting point greater than 150° C. Such nanoparticulate compositions can be prepared by dispersing the compounds of the invention in a liquid dispersion medium, and wet grinding the compound in the presence of rigid grinding media and a surface modifier to form the nanoparticles. Alternatively, the surface modifier can be contacted with the compound after attrition. Preferred surface modifiers include nonionic surfactants.

In preferred embodiments, the surface modifier is a high molecular weight nonionic surfactant. Preferred surfactants include poloxamers such as Pluronic® F68 and F108, which are block copolymers of ethylene oxide and propylene oxide, poloxamines, such as Tetronic® 908 (also known as Poloxamine 908), which is a tetrafunctional block copolymer derived from sequential addition of propylene oxide and ethylene oxide to ethylenediamine, and dialkyl esters of sodium sulfosuccinic acid, such as dioctylsulfosuccinate sodium (DOSS). The concentrations of the surface modifier can vary from about 0.1–75%, preferably 1–60%, and more preferably 10–30% by weight based on the total combined weight of the contrast agent and surface modifier.

In preferred embodiments, the x-ray contrast composition in the form of surface modified nanoparticles can be associated with a cloud point modifier to further enhance stability during steam heat autoclaving, i.e., the cloud point modifier can reduce particle aggregation during heat sterilization. Preferred cloud point modifiers include nonionic cloud point modifiers, such as polyethylene glycols such as PEG 400, propylene glycol, ethanol, hydroxypropylcyclodextrin, and glycerol; ionic cloud point modifiers, such as those described in U.S. Pat. No. 5,298,262 including dialkylesters of sodium sulfosuccinic acid such as the dioctylester of sodium sulfosuccinic acid (DOSS); and charged phospholipids, such as diacylphosphatidyl glycerol and dimyristoylphosphatidyl glycerol. The cloud point modifier can be present in an amount of 0.005–50%, preferably 0.01–30% and more preferably 0.05–20% by weight based on the total weight of the x-ray contrast composition.

The x-ray contrast compositions of this invention comprise the above-described compounds, preferably in the form of particles, and a physiologically acceptable carrier therefor. For example, the particles can be dispersed in an aqueous liquid which serves as the carrier for the x-ray contrast agent. Other suitable carriers include liquid carriers such as mixed aqueous and nonaqueous solvents, such as alcohol; gels; gases, such as air; and powders.

The x-ray contrast composition can comprise from about 1–99.9, preferably 2–45 and more preferably 10–25% by weight of the above-described particles, the remainder of the composition being the carrier, additives and the like. Compositions up to about 100% by weight of the particles are contemplated when the composition is in a lyophilized form.

The dose of the contrast agent to be administered can be selected according to techniques known to those skilled in the art such that a sufficient contrast enhancing effect is obtained. Typical doses can range from 20 to 350 mg of iodine per kilogram of body weight of the subject for many imaging applications. For some applications, e.g., lymphography, lower doses, e.g., 0.5–20 mg I/kg, can be effective. For blood pool imaging, the dose can range from 50 to 350 mg of iodine per kilogram of body weight.

The x-ray contrast composition can contain one or more conventional additives used to control and/or enhance the properties of the x-ray contrast agent. For example, thickening agents such as dextran or human serum albumin, buffers, viscosity regulating agents, suspending agents, peptizing agents, anti-clotting agents, mixing agents, and other drugs and the like can be added. A partial listing of certain specific additives includes gums, sugars such as dextran, human serum albumin, gelatin, sodium alginate, agar, dextrin, pectin and sodium carboxymethyl cellulose. Such additives, surface active agents, preservatives and the like can be incorporated into the compositions of the invention.

A method for diagnostic imaging for use in medical procedures in accordance with this invention comprises administering to the body of a test subject in need of an x-ray an effective contrast producing amount of the above-described x-ray contrast composition. In addition to human patients, the test subject can include mammalian species such as rabbits, dogs, cats, monkeys, sheep, pigs, horses, bovine animals and the like. Thereafter, at least a portion of the body containing the administered contrast agent is exposed to x-rays to produce an x-ray image pattern corresponding to the presence of the contrast agent. The image pattern can then be visualized. For example, any x-ray visualization technique, preferably, a high contrast technique such as computed tomography, can be applied in a conventional manner. Alternatively, the image pattern can be observed directly on an x-ray sensitive phosphor screen-silver halide photographic film combination.

The compositions of this invention can be administered by a variety of routes depending on the type of procedure and the anatomical orientation of the tissue being examined. Suitable administration routes include intravascular (arterial or venous) administration by catheter, intravenous injection, rectal administration, subcutaneous administration, intramuscular administration, intralesional administration, intrathecal administration, intracisternal administration, oral administration, administration via inhalation, administration directly into a body cavity, e.g., arthrography, and the like.

In addition to preferred applications, i.e., for blood pool, liver, spleen and lymph node imaging, the x-ray contrast compositions of this invention are also expected to be useful as contrast agents for any organ or body cavity. For example, the compositions of this invention are expected to be useful as angiographic contrast media, urographic contrast media, myelographic contrast media, gastrointestinal contrast media, cholecystographic and cholangiographic contrast media, arthrographic contrast media, hysterosalpingographic contrast media, oral contrast media and bronchographic contrast media.

The following examples further illustrate the invention.

EXAMPLE 1

Synthesis of WIN 67722 (6-Ethoxy-6-oxohexyl 3,5-bis (acetylamino) -2, 4, 6-triiodobenzoate)

Sodium diatrizoate (16.1 g, 25.3 mmol) was dissolved in 180 ml of dry dimethylformamide and to this solution was added, in one portion, ethyl 6-bromohexanoate (4.5 ml, 25.3 mmol). The reaction mixture was stirred for 12 hr at ambient temperature and then poured into 1.6 l of ice-water with stirring. The resulting white precipitate was collected by filtration, dissolved in 1:1 ethanol-ethyl acetate and the solution was treated sequentially with magnesium sulfate, decolorizing charcoal and then filtered through a short pad of silica gel. The filtrate was concentrated to dryness and dried to give 16 g (84%) of the desired product. Recrystallization from methanol-water gave analytically pure material, mp 235°–238° C. (decomp. at 275° C.); MS:M$^+$756. The $^1$H-NMR (300 MH$_z$) spectral data was consistent with the desired product. Calculated for $C_{19}H_{23}I_3N_2O_6$: C 30.18, H 3.07, I 50.35, N 3.70; Found: C 30.26, H 2.88, I 50.40, N 3.65.

EXAMPLE 2

Synthesis of WIN 67954 (5-Ethoxy-5-oxopentyl 3,5-bis(acetylamino)-2,4,6-triiodobenzoate)

To a stirred solution of sodium diatrizoate (59.0 g, 92.8 mmol) in 350 ml of dry DMF was added ethyl 5-bromovalerate (14.7 ml, 92.8 mmol) in two portions and the resulting solution was stirred at ambient temperature for 12 hr. The reaction mixture was poured into 3.5 l of water and the resulting white precipitate was collected, washed with ether and then air dried. The crude product was dissolved in acetonitrile-ethanol (5:2), filtered through a pad of silica gel and the filtrate was evaporated to give a solid (67 g, 97%). Recrystallization from methanol-water gave analytically pure product (mp 237°–239° C.) after drying under high vacuum; CI-MS: MH$^+$743. The $^1$H-NMR (300 MH$_z$) spectral data was consistent with the desired product. Calculated for $C_{18}H_{21}I_3N_2O_6$; C 29.13, H 2.85, I 51.30; Found: C 29.13, H 2.78, I 51.15, N 3.75.

EXAMPLES 3–20

In a manner similar to the procedures described in Examples 1 and 2 above, the compounds set forth in the Table above were prepared. In each case, the MS and spectral data (300 MH$_z$) were consistent with the desired product.

Compounds of the invention and a prior art compound were tested as summarized in the table below. Solubility was tested in water and is expressed as mg/ml. Esterase stability is expressed as the product to substrate ratio calculated after a ten minute exposure of a compound of the invention to rabbit liver esterase.

| WIN | Solubility µg/ml | Esterase Stabilty |
|---|---|---|
| 12901 | 18 | 17.8 |
| 68061 | 86 | 13.3 |
| 67954 | 16 | 3.2 |
| 67722 | 2 | 2.7 |
| 68136 | 1 | 0.2 |
| 68166 | 1 | 0.35 |

Compound WIN 12901 corresponds to the compound of GB 866,184, formula C, wherein $R_1$ is H, $R_2$ is acetyl, $R_3$ is acetylamino and $R_4$ is ethyl.

The testing demonstrates that the lengths of the methylene chain separating the two ester groups is important in conferring both low solubility and high resistance to esterase degradation. It is expected that analogs containing additional carbon atoms between the ester groups would exhibit low solubility and high resistance to esterase degradation.

The corresponding acids of the above-described esters, i.e., wherein $R^5$=H can be prepared by conventional techniques known in the art. Such acids and salts thereof are useful as wetting agents and/or as surface modifiers in x-ray contrast compositions, particularly in nanoparticulate x-ray contrast compositions.

The invention has been described in detail with particular reference to certain preferred embodiments thereof, but it will be understood that variations and modifications can be effected within the spirit and scope of the invention.

We claim:

1. A compound having the structure

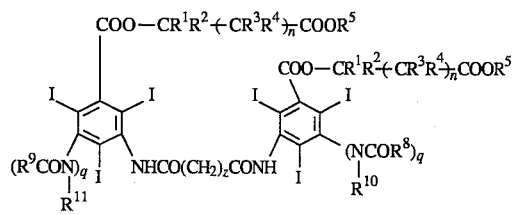

wherein z is an integer from 1 to 10; q is 0 or 1; n is an integer from 1 to 20;

$R^1$ and $R^2$ are independently H, alkyl, fluoroalkyl, cycloalkyl, aryl, aralkyl, alkoxy or aryloxy;

$R^3$ and $R^4$ are independently H, alkyl, fluoroalkyl, cycloalkyl, aryl, aralkyl, alkoxy, aryloxy, halogen, hydroxy or acylamino;

$R^5$ is H, alkyl, cycloalkyl, aryl, aralkyl, alkoxyalkyl or acetamidoalkyl;

$R^8$ and $R^9$ are independently alkyl, cycloalkyl, aryl or aralkyl; and $R^{10}$ and $R^{11}$ are independently H or —COR$^8$; said compound comprising at least 40% iodine by weight.

2. The compound of claim 1 wherein $R^1$–$R^4$ are H, $R^5$ is $C_2H_5$ n is 2–4, q is 0, and z is 4.

3. An x-ray contrast composition comprising the compound of claim 1.

4. The x-ray contrast composition of claim 3 further including a pharmaceutically acceptable carrier.

5. A method of medical x-ray diagnostic imaging which comprises administering to the body of a mammal a contrast effective amount of the x-ray contrast composition of claim 3.

6. The compound having the structure:

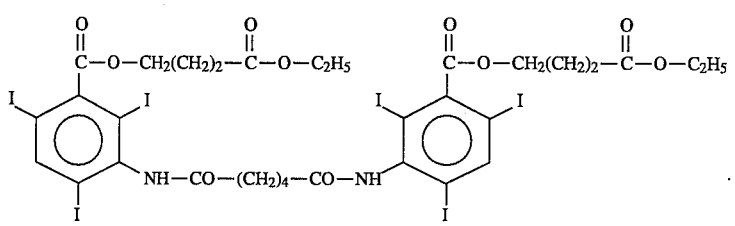

7. The compound having the structure:

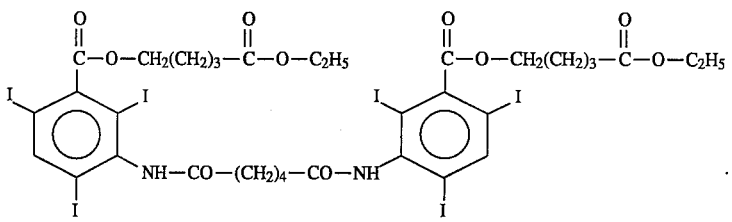

8. The compound having the structure:

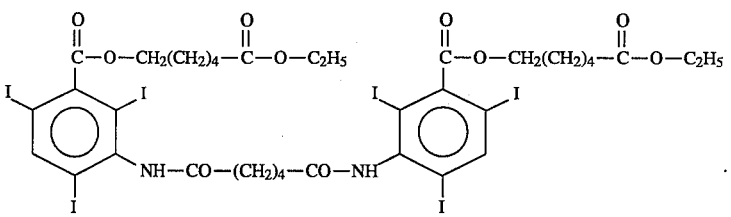

9. An uncharged compound having the structure:

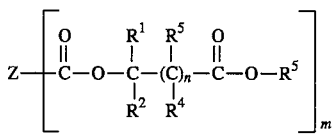

wherein Z is the residue of a polyiodinated aromatic acid;
m is 2, 3 or 4;
n is an integer from 4 to 20;

$R^1$ and $R^2$ are independently H, alkyl, fluoroalkyl, cycloalkyl, aryl, aralkyl, alkoxy, or aryloxy;

$R^3$ and $R^4$ are independently H, alkyl, fluoroalkyl, cycloalkyl, aryl, aralkyl, alkoxy, aryloxy, halogen, hydroxy or acylamine; and $R^5$ is H, alkyl, cycloalkyl, aryl, aralkyl, alkoxyalkyl or acetamidoalkyl, said compound comprising at least 40% iodine by weight.

* * * * *